United States Patent
Gambale (10) Patent No.: US 6,277,082 B1
(45) Date of Patent: Aug. 21, 2001

(54) ISCHEMIA DETECTION SYSTEM

(75) Inventor: Richard A. Gambale, Tyngsboro, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/358,947

(22) Filed: Jul. 22, 1999

(51) Int. Cl.[7] .................................................. A61B 5/00
(52) U.S. Cl. ............................................................ 600/549
(58) Field of Search .................................... 600/549, 117

(56) References Cited

U.S. PATENT DOCUMENTS

| | | |
|---|---|---|
| 3,680,544 | 8/1972 | Shinnick et al. |
| 4,894,057 | 1/1990 | Howes. |

(List continued on next page.)

FOREIGN PATENT DOCUMENTS

| | | |
|---|---|---|
| 197 03 482 | 1/1997 | (DE). |
| 0 490 459A1 | 6/1992 | (EP). |
| 0 717 969A2 | 6/1996 | (EP). |
| 0 830 873A2 | 3/1998 | (EP). |
| 0 853 921A2 | 7/1998 | (EP). |
| 0 953 320A2 | 11/1999 | (EP). |
| WO 90/06723 | 6/1990 | (WO). |
| WO 94/27612 | 12/1994 | (WO). |
| WO 95/33511 | 12/1995 | (WO). |
| WO 96/20698 | 7/1996 | (WO). |
| WO 97/42910 | 7/1997 | (WO). |
| WO 97/38730 | 10/1997 | (WO). |
| WO 97/45105 | 12/1997 | (WO). |
| WO 98/23228 | 6/1998 | (WO). |
| WO 98/29148 | 7/1998 | (WO). |
| WO 98/46115 | 10/1998 | (WO). |
| WO 99/21510 | 5/1999 | (WO). |
| WO 99/53863 | 10/1999 | (WO). |

OTHER PUBLICATIONS

Sen, P.K. et al., "Transmyocardial Acupuncture–A New Approach to Myocardial Revascularization", *Journal of Thoracic and Cardiovascular Surgery,* vol. 50, No. 2, Aug. 1965, pp. 181–189.

Mirhoseini, M. et al., "Revascularization of the Heart by Laser", *Journal of Microsurgery,* vol. 2, No. 4, Jun. 1981, pp. 253–260.

Hescheler, J. et al., Embryonic Stem Cells: A Model to Study Structural and Functional Properties in Cardiomyogenesis, *Cardiovascular Research 36* (1997) pp. 149–162.

Schumacher, B. et al., "Induction of Neoangiogenesis in Ischemic Myocardium by Human Growth Factors", *Circulation,* 1998;97:645–650.

Okada, Robert D. et al., "Tc–HL91 'Hot Spot' Detection of Ischemic Myocardium in Vivo by Gamma Camera Imaging", *Circulation,* 1998;97:2557–2566.

Gaughan, Richard, "Thermal Imaging is Gaining Acceptance as a Diagnostic Tool" *Biophotonics Int'l.,* Nov./Dec. 1998, pp. 48–53.

Primary Examiner—John P. Lacyk
Assistant Examiner—Brian Szmal
(74) Attorney, Agent, or Firm—Kirkpatrick & Lockhart LLP (57) ABSTRACT

The present invention provides devices and methods for detection of ischemic biological tissue by temporarily altering the temperature of the tissue and then monitoring the thermal profile of the tissue as it returns to normal temperature. Tissue areas of slower response time correspond to areas of reduced blood flow (ischemia). Several embodiments are disclosed. In one embodiment a fiber optic device is used to record thermal images of the tissue after it has been cooled by introduction of a cool fluid. In another embodiment detection is accomplished through the use of thermal sensors to monitor the temperature profile of the tissue after the temperature change.

32 Claims, 3 Drawing Sheets

U.S. PATENT DOCUMENTS

| | | |
|---|---|---|
| 4,904,264 | 2/1990 | Scheunemann . |
| 5,180,366 | 1/1993 | Woods . |
| 5,366,493 | 11/1994 | Scheiner et al. . |
| 5,380,316 | 1/1995 | Aita et al. . |
| 5,389,096 | 2/1995 | Aita et al. . |
| 5,429,144 | 7/1995 | Wilk . |
| 5,562,922 | 10/1996 | Lambert . |
| 5,655,548 | 8/1997 | Nelson et al. . |
| 5,690,643 | 11/1997 | Wijay . |
| 5,755,682 | 5/1998 | Knudson et al. . |
| 5,769,843 | 6/1998 | Abela et al. . |
| 5,779,365 * | 7/1998 | Takaki .................................. 600/549 |
| 5,797,398 * | 8/1998 | Bowman .............................. 600/549 |
| 5,810,836 | 9/1998 | Hussein et al. . |
| 5,853,409 * | 12/1998 | Swanson et al. ..................... 600/549 |
| 5,935,075 | 8/1999 | Casscells et al. . |
| 5,971,993 | 10/1999 | Hussein et al. . |
| 5,980,514 | 11/1999 | Kupiecki et al. . |
| 5,980,548 | 11/1999 | Evans et al. . |
| 6,010,449 * | 1/2000 | Selmon et al. ....................... 600/117 |
| 6,045,565 | 4/2000 | Ellis et al. . |
| 6,053,924 | 4/2000 | Hussein . |

* cited by examiner

ISCHEMIA DETECTION SYSTEM

FIELD OF THE INVENTION

The invention relates to devices and methods for the detection and treatment of ischemic tissue.

BACKGROUND OF THE INVENTION

Ischemia is a condition of blood deprivation that affects biological tissue, typically because of a blockage or constriction of the blood vessels supplying the tissues in question. Myocardial ischemia is a common complication of coronary artery disease due to narrowing of the blood vessels because of the accumulation of plaque. In the absence of proper treatment, ischemic tissue may become infarcted (necrotic). Myocardial infarction is a serious occurrence and may result in death. Proper treatment of ischemic areas continues to be a challenge for medical science.

In recent years the concept of revascularizing the myocardium has become the subject of increasing study. If the tissue has remained viable despite the previous deprivation of blood, revascularization, or the restoration of blood flow, to dormant or hibernating tissue can restore the muscle's normal function. The technique of revascularizing the myocardium by creating passages into the tissue through which blood may flow has become known as Transmyocardial Revascularization (TMR). Creating channels part of the way through the myocardium is believed to permit blood from the ventricle to reach sinusoids within the muscle. Early researchers reported promising results by piercing the myocardium to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2, August 1965, pp. 181–189. An alternative method involves the use of a laser to form the channels with heat energy. Mirhoseini, M. et al., "Revascularization of the Heart by Laser", *Journal of Microsurgery*, Vol. 2, No. 4, June 1981, pp. 253–260. The use of a catheter-based apparatus to create laser-made channels for TMR is disclosed in U.S. Pat. No. 5,769,843 (Abela). Abela '843 also discloses the use of a magnetic navigation system to guide the catheter to the desired position within the heart. U.S. Pat. Nos. 5,380,316 and 5,389,096 (Aita) disclose another approach to a catheter-based system for TMR.

Although there has been some published recognition of the desirability of performing TMR in a non-laser catheterization procedure, there does not appear to be evidence that such procedures have been put into practice. U.S. Pat. No. 5,429,144 (Wilk) discloses inserting an expandable implant within a preformed channel created within the myocardium for the purposes of creating blood flow into the tissue from the left ventricle. Performing TMR by placing stents in the myocardium is also disclosed in U.S. Pat. No. 5,810,836 (Hussein et al.). The Hussein patent discloses several stent embodiments that are delivered through the epicardium of the heart, into the myocardium and positioned to be open to the left ventricle.

Recently, researchers have examined the possibility of treating diseased myocardial tissue with therapeutic substances or cell therapy to revive the tissue. For example stem cells, as well as cell components, such as DNA and proteins, are considered to hold potential as a promising treatment for diseased tissue regions. It has been reported that stem cells may be capable of transforming into a highly specialized cells of a given organ in which they are placed. J. Hescheler et al., Embryotic *Stem Cells: A Model To Study Structural And Functional Properties In Cardiomyogenesis*, Cardiovascular Research 36 (1997) 149–162. Addition of such cells to the tissue of an organ may serve to initiate growth of the tissue of that organ. Also, encouraging blood vessel growth to provide new supplies of oxygenated blood to a region of tissue has been reported as a potential remedy for a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation*, 1998; 97:645–650.

Because accurate diagnosis and identification of ischemic areas is essential to proper treatment, there is a need for medical techniques that can pinpoint ischemic regions of the myocardium. Previous methods of ischemic tissue identification have relied on various techniques mostly relying on visual identification of the ischemic region. In identifying ischemic areas of myocardial tissue of the heart, movement of the heart muscle is observed for abnormal motion. Such visual methods can require extensive x-ray imaging. PET scanning, Thalium 201, and magnetic resonance imaging are examples of current visual methods of identifying ischemic regions. Recently, Gamma Camera Imaging has been reported as a potentially useful tool in identifying ischemic myocardial tissue. Okada et al., "Tc-HL91 "Hot Spot" Detection of Ischemic Myocardium In Vivo by Gamma Camera Imaging" Circulation, 1998;97:2557–2566.

It would be desirable to provide an accurate yet simple and cost effective method of ischemia detection and identification that could be easily combined with a procedure for treating the identified ischemic region. It is an object of the present invention to provide such a system.

SUMMARY OF THE INVENTION

The present invention provides a device for the detection of ischemia in biological tissue that uses the thermal response of the tissue following alteration of its temperature to detect the difference between normal and ischemic tissue. Ischemia causes a reduced rate of blood flow within the tissue that directly affects the recovery time of tissue returning to a normal temperature after the initial temperature is altered. Blood regulates the temperature of tissue through which it circulates at normal body temperature. Because ischemic tissue has a decreased rate of blood flow, it returns to normal body temperature more slowly after a temperature change than does healthy tissue with adequate blood flow. The variation in thermal recovery time can be observed whether the tissue has been warmed above or cooled below normal temperatures.

In a method of the present invention, a monitoring catheter is navigated through a predetermined path in the patient's vascular system, usually via the femoral artery of the patient to reach the affected tissue, for example, the myocardium of the heart. The method of identifying ischemia comprises temporarily altering the temperature of a section of the tissue to be either warmer or colder than normal, and then recording and displaying its thermal profile over time as it returns to normal temperature. Temperature data are recorded at the distal end of the catheter, transmitted to the proximal end of the catheter, and displayed outside the patient to be viewed by the physician. Ischemic tissue, which is slower to return to normal temperature, is identified when areas are measured that respond more slowly than adjacent areas that have been previously measured or more slowly than otherwise expected.

In one embodiment of the invention the method of temperature alteration is performed by delivering cool fluid through a lumen of the monitoring catheter. After the fluid is delivered to cool an area of tissue, the thermal profile of the tissue is recorded by an optical fiber and displayed on a monitor outside the patient as a thermal image showing the regions of different temperature in varying colors. Alternatively, fluid warmer than normal body temperature can be delivered to warm the tissue area so that its cooling response time can be observed.

In another embodiment, the temperature alteration is also performed by delivering cool or warm fluid through the catheter. However, after temperature alteration, tissue temperature is measured by thermal conductor sensors brought into contact with the tissue. For example, an obturator adapted to pierce the myocardium having at least one thermal sensor, such as a thermocouple at its tip, is introduced via the monitoring catheter and brought into contact with the tissue. The thermal sensors on the obturator sense and transmit the temperature data of the tissue to the proximal end of the catheter through electrical leads extending within a lumen of the catheter. The proximal ends of the leads are joined to a temperature display so that the temperature of the tissue location over time can be viewed and a profile constructed. A variation of this embodiment accomplishes the temperature change of the tissue through direct conduction heating by the sensors against the tissue. Heat is created by the resistance of electrical current transmitted to the sensors on the obturator through the leads.

In another embodiment of the invention, the monitoring catheter is provided having retractable radially projecting fingers, that extend from the distal end of the catheter and have temperature sensors that contact the tissue. Temperature alteration may be effected through either conductive heating by the sensors, or by perfusing the tissue with cool fluid delivered through a catheter lumen.

In all embodiments, detection of an ischemic area of tissue may be followed by a treatment, which may include the implantation of an angiogenic implant alone or in conjunction with a therapeutic agent, such as a growth factor to promote angiogenesis or a cell or gene therapy substance to initiate regeneration of the subject tissue. In such cases, the obturator is adapted to penetrate the tissue in order to facilitate the placement of the angiogenic implant into the tissue alternatively the treatment may comprise creation of channels in the ischemic region by mechanical or laser energy. The progress of recovery of the ischemic tissue also may be monitored over time by using the monitoring catheter as described herein to observe the thermal response of the tissue after treatment.

It is an object of the invention to provide a method of detecting ischemia in the myocardium by temporarily altering the temperature of the tissue, then monitoring the temperature of the tissue to determine whether its recovery time to normal body temperature indicates normal or ischemic tissue.

It is another object of the invention to provide a method for targeting the placement of an angiogenic implant by providing and using a device capable of detecting ischemia in tissue.

It is another object of the invention to provide a device for detecting ischemia in the myocardium of a patient by monitoring the temperature of the tissue after perfusion with a fluid bolus of a temperature cooler or warmer than normal body temperature.

It is another object of the invention to provide a device for detection of ischemia in the myocardium of a patient that uses an optical fiber and infrared detector to create a thermal image of the tissue that can illustrate temperature differences between areas of the tissue.

It is another object of the invention to provide a device for detection of ischemia in the myocardium of a patient that utilizes an obturator having at least one thermal sensor adjacent to its distal tip to monitor the temperature response of the myocardial tissue after either perfusion with a fluid bolus or direct heating of the tissue.

It is another object of the invention to provide a method of detecting ischemia that involves using a catheter based apparatus that can monitor the thermal response of tissue after the device has been used to alter the temperature of the tissue.

It is still another object of the invention to provide a method for monitoring the progress of recovery of tissue area that has been previously treated for ischemia.

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENTS

The present invention provides a device for detecting ischemia in tissue, by temporarily altering the temperature of the tissue and then monitoring the tissue's thermal response as it returns to normal body temperature. It is expected that, ischemic tissue areas will return to normal body temperature more slowly than healthy tissue areas because of the decreased circulation of blood in the ischemic tissue.

Preferred embodiments of the present invention use a monitoring catheter configured to be navigated through the vasculature to reach the tissue that will be examined for ischemia. Though the devices and methods of the present invention can be used to detect ischemia in various areas of the body, it is expected to be particularly useful for detecting ischemia areas of myocardial tissue of the heart. Some embodiments of the present invention are also configured to treat the ischemic region after it is located by implanting an angiogenic implant or delivering therapeutic substances or cells or gene therapy material or delivering both a device and a substance. Examples of angiogenic devices are described in detail in pending U.S. application Ser. No. 09/323,808 filed Jun. 9, 1999; Ser. No. 09/299,795 filed Apr. 26, 1999; Ser. No. 09/162,547 filed Sep. 29, 1998; and Ser. No. 09/164,163 filed Sep. 30, 1998, which are incorporated by reference in their entirety herein.

Figure 1:
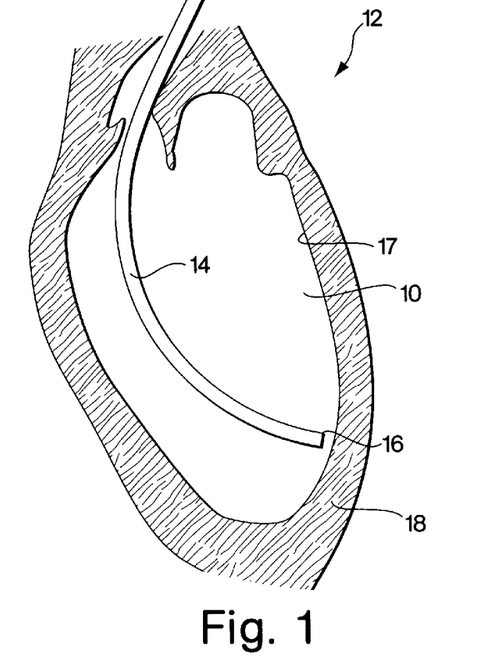
FIG. 1 is an illustration of a detection catheter of the invention entering the left ventricle of a patient's heart from the coronary artery.

FIG. 1 shows, in diagrammatic section, the left ventricle 10 of a human heart 12 having inserted within it a monitoring catheter 14. The distal end 16 of the catheter is configured to observe the thermal response of an area of tissue as will be described in detail below. In FIG. 1, the distal end 16 of the catheter is positioned adjacent tissue of the myocardium 18 to be examined.

Figure 2:
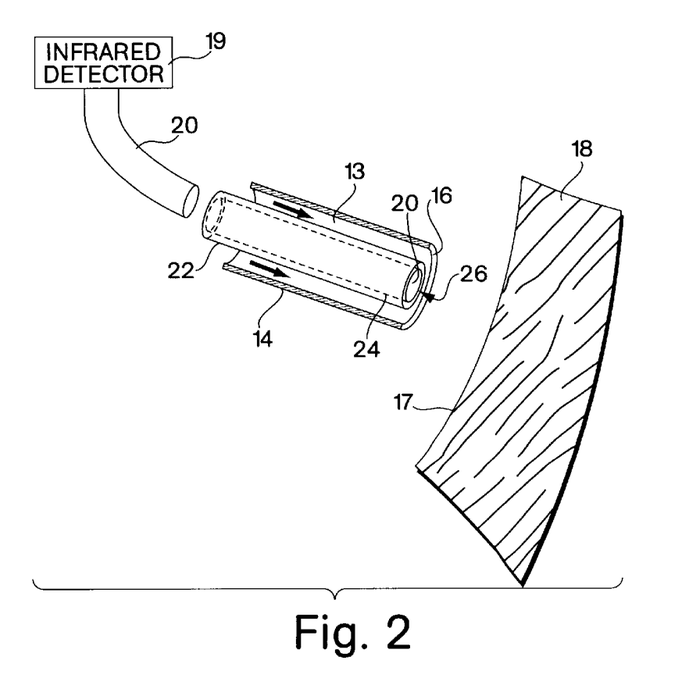
FIG. 2 is an illustration of an ischemia detecting catheter of the present invention having an optical fiber for imaging the thermal profile of a section of the patient's myocardium.

FIG. 2 shows a preferred embodiment of the invention in which the monitoring catheter 14 is configured to monitor thermal response of areas of tissue through the use of an optical fiber 20 and infrared detector 19 to create a thermal image of the finite section of the tissue. The catheter 14 is shown positioned adjacent to a section of the myocardium 18 to be examined. The catheter first may be navigated to the tissue location through a guide catheter and over a deflectable tip steerable guidewire (not shown) by techniques well known in the art. The guidewire is removed from a lumen 13 of the catheter 14 and replaced with a infrared fiber optic catheter 22. The fiber optic catheter 22 has a lumen 24 in which is placed the optical fiber 20 (shown in phantom). The distal tip 26 of the optical fiber 20 is capable of monitoring from a distance the thermal energy originating from a portion of the endocardial surface 17 of the myocardium 18.

In the practice of the invention, the temperature of a section of the endocardium 17 can be altered by perfusing the ventricle 10 with fluid delivered through the lumen 13 of the catheter 14 that is at a temperature either above or below normal body temperature. After the temperature of the endocardium has been altered, certain regions of tissue return to normal body temperature more quickly than others. As temperature of the tissue returns to normal, multiple points on the tissue are monitored over a period of time by the distal tip 26 of the optical fiber 20. Thermal energy information, reflecting the temperature profile of the tissue, is received by the optical fiber 20 and is transmitted along its length proximally to an infrared detector 19 outside the patient. The infrared detector uses the data to create a thermal image of the tissue area which can be displayed on an electronic video screen and observed by the physician to identify ischemic regions. The use of infrared technology to display an image of a thermal profile of mammalian tissue is described in: Gaughan "Thermal Imaging Is Gaining Acceptance as a Diagnostic Tool" Biophotonics Int'l, November/December 1998, 48–53, the entirety of which is incorporated by reference.

The profile of the thermal response of normal myocardial tissue of the can be identified by an experienced physician. Knowledge of the thermal profile of normal tissue makes it possible to distinguish both hibernating ischemic tissue and infarcted tissue. Infarcted tissue would be characterized by a thermal profile indicating a slower return to body temperature then is exhibited by normal tissues. Hibernating ischemic tissue should respond in a manner between normal and infarcted tissue. If the monitored tissue is shown to be normal, the catheter would be repositioned to monitor another region. In the next position the above described analysis is repeated. When the thermal profile indicates ischemic tissue, the fiber optic catheter 22 can be removed from the lumen 13 of the monitoring catheter 14 and replaced by a treatment device, such as a laser catheter or an angiogenic implant or agent delivery catheter inserted to precisely treat the ischemic region that has been detected. Steerable angiogenic implant delivery catheters configured to be operated in regions such as the left ventricle of the heart are described in pending U.S. patent application Ser. No. 09/073,118 filed May 5, 1998; Ser. No. 09/164,173 filed Sep. 30, 1998; and Ser. No. 09/164,884 filed Sep. 30, 1998, which are incorporated by reference herein in their entirety.

Figure 3:
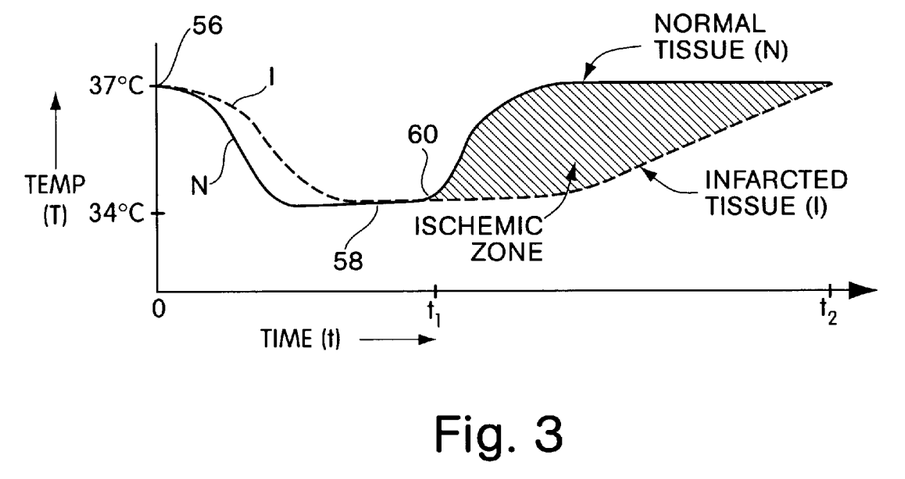
FIG. 3 is a graph showing the thermal response cycles of normal and ischemic tissue as a function of time after contact with fluid at below normal body temperature.

FIG. 3 shows a graphical representation of the thermal response profile of two sections of tissue, one normal and one ischemic, after temperature alteration and monitoring using the invention. The temperature (T) of normal and infarcted tissue points are shown as a function of time (t). The dotted curve line represents the response of a section of infarcted tissue while the solid curve line represent the response of a normal section of tissue. Before temperature alteration (t=0), the temperature of both infarcted and normal tissue is identical at point 56. Temperature alteration (cooling in this example) is indicated by the marked temperature reduction represented at trough area 58. After the trough 58, the differences in response between normal and infarcted tissue become evident at point 60 ($t=t_1$) where a section of normal tissue begins to recover from the temperature reduction, shown by increasing temperature, while infarcted tissue remains cool. Between $t_1$ and $t_2$ the temperature of the normal section of tissue remains higher than the temperature of the infarcted tissue. Any tissue section found to have a thermal profile represented by a curve that lies beneath the curve of the normal tissue section would be considered to be ischemic The ischemic zone is indicated in the graph by the shaded region 59.

Figure 4:
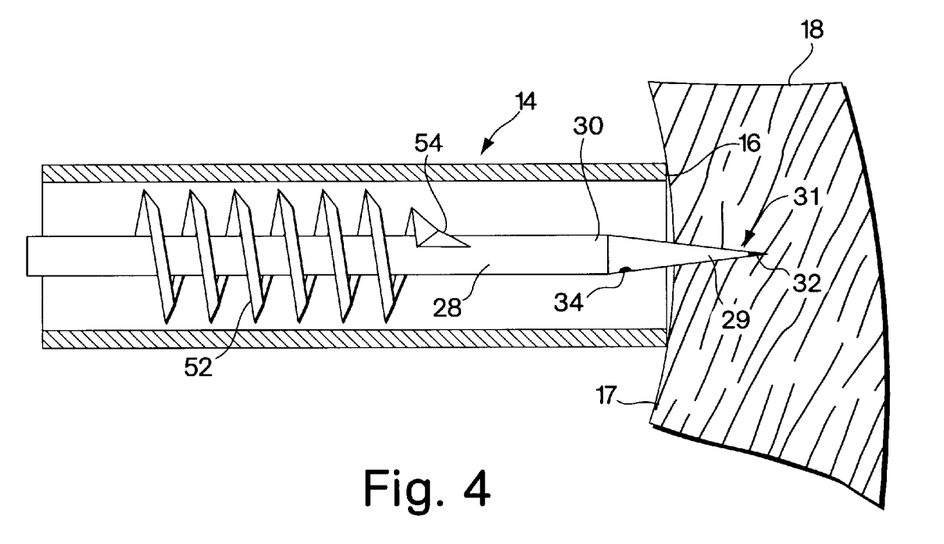
FIG. 4 is an illustration of an ischemia detecting catheter of the invention using an obturator having thermal sensors at its distal end.

FIG. 4 shows a second embodiment of the invention that uses conductive temperature sensors rather infrared technology to monitor temperature of the tissue. The use of conductive temperature sensors may provide a more economical alternative to infrared technology. Sensors 32 and 34 may be affixed to an elongate shaft 28, hollow or solid, that is inserted through the lumen 13 of a monitoring catheter 14, or other suitable guide catheter, that has been previously navigated to the intended tissue location, such as adjacent the myocardium 18 of the heart. The distal end 30 of the shaft 28 is extended from the distal end 16 of the monitoring catheter and placed in direct contact with the endocardium 17 and possibly into the myocardium 18. Conductive sensors 32 and 34 may include thermocouples, thermistors or resistance temperature detectors. The sensors are placed in contact with the tissue and receive heat from the tissue by conduction.

Figure 5:
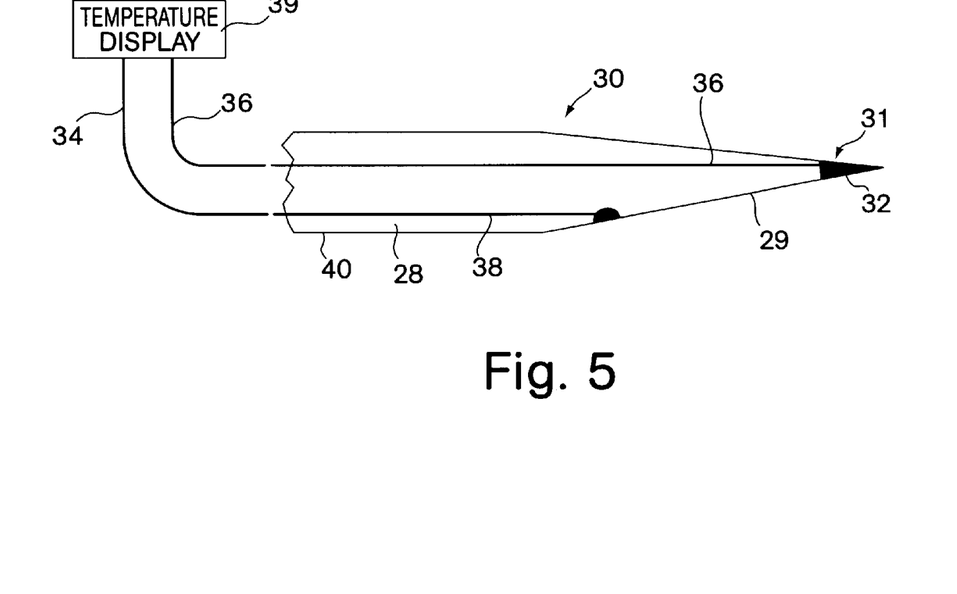
FIG. 5 is a detailed illustration of the distal end of the obturator shown in FIG. 4.

As shown in FIG. 5, leads 36 and 38, which may comprise wires are joined to the sensors and extend along or within the shaft to transmit temperature data to the proximal end of the shaft outside the patient. The proximal end of the leads may be joined to a temperature display 39 so that the information can be clearly monitored by the user. In a preferred embodiment, the distal end of the shaft, which holds the temperature sensors, is configured as an obturator 29. The obturator is configured to pierce the tissue being monitored so that an angiogenic device may be implanted or agent inserted into the tissue if ischemia is detected. The distal tip 31 of the obturator 29 is equipped with a thermal sensor 32 capable of measuring the temperature of the tissue at the tissue surface or at a given depth in the tissue, if the obturator tip pierces the tissue. In use, the temperature of the tissue may be altered by fluid delivered through the monitoring catheter as described above. Alternatively, heat generated at the sensors from an electrical current passed through the leads is used to elevate the temperature of a section of the myocardium 18. Current is transmitted along the main lead wire 36 and the secondary lead wire 38, causing the main temperature sensor 32 and secondary sensor 34, respectively, to become transiently heated and in turn to elevate the temperature of a local area of the myocardium 18. After a short period of heating, current is discontinued to the primary 36 and secondary 38 lead wires. The main sensor 32 and the secondary sensor 34 then measure the temperature of the tissue and relay the data through the leads to the temperature display to create a profile of the response measured at the two tissue areas in contact with the sensors. In an alternative embodiment the metallic outer shell 40 of the obturator 28 may serve as a lead if it is joined to a conductive shaft or proximally extending lead.

Figure 6:
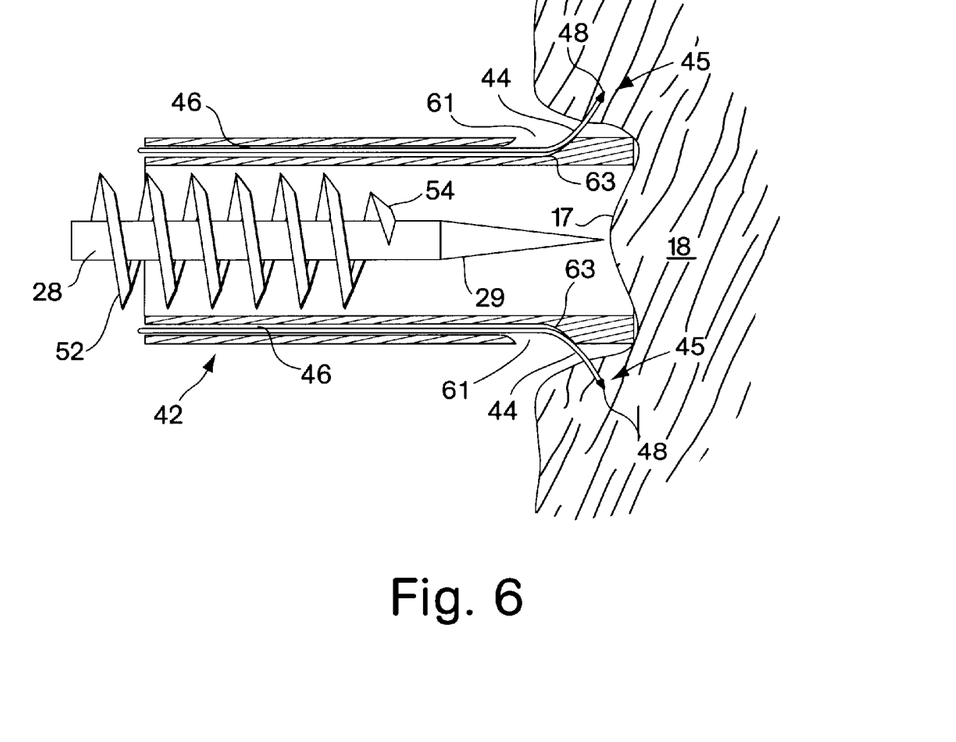
FIG. 6 is a sectional view of the distal tip of the catheter shown in FIG. 4.

FIG. 6 shows another embodiment of the ischemia detection system. The illustration is a sectional view of the distal portion of a latching monitoring catheter 42 having thermal sensing radial fingers 44 that are slidably received within secondary lumens 46 coextensive with the catheter 42. In use, after the distal end of the latching catheter is navigated to be in contact with the tissue surface to be monitored, such as the endocardium 17, the fingers 44 are advanced distally and caused to project radially as they emerge through anvil ports 61 at the distal ends of the secondary lumens 46. The curved shape of the anvil ports causes the flexible fingers to curve and extend radially outward, piercing tissue that has gathered around the side wall of the latching catheter after being poked by the distal end of the catheter. The distal tips 45 of the radial fingers 44 have thermocouple junctions 48 that contact and pierce the endocardium 17. Current is transmitted through the fingers 44 to the distal tips 45 to transiently heat a section of the myocardium. Alternatively, fluid may travel through a primary lumen 43 catheter 42 to perfuse a section of the myocardium 18. Following such a temperature alteration, the radial sensing fingers 44 transmit temperature data collected from their contact points in the myocardium 18 so that a thermal profile can be created and ischemic regions identified.

Following detection of an ischemic area of the tissue, the ischemia detection device can be used to facilitate treatment of the identified ischemic region. An angiogenic implant 52 having a tip 54 adapted to help penetrate the endocardium 17 may be carried over the obturator shaft 28 that slides within the monitoring catheter lumen 13 as shown in FIGS. 4 and 6. After ischemia detection, the implant 52, such as flexible helical coil configured to promote angiogenesis may be implanted into the tissue for treatment of the ischemia. Alternatively or in addition to the implant, therapeutic agents may be delivered at the site of the ischemic tissue, preferably delivered into the tissue by injection either through the piercing obturator head 29 modified to have a delivery lumen extending therethrough and distal delivery port, or through a hypodermic needle based device subsequently introduced to the site through the monitoring catheter. The agents may be in any flowable form such as a liquid or gel, or may comprise a degradable solid in a pellet form. Growth factors useful in promoting angiogenesis may used as an agent. Also cell therapies such as stem cells, precursor cells or skeletal myoblasts may be delivered to the ischemic region to initiate regeneration of the tissue.

Laser energy may also be used in the ischemia treatment. In the case of ischemic myocardial tissue, the optical fiber present in the infrared sensing embodiments may be used to transmit laser energy suitable for controlably creating channels into the tissue. The channels may provide relief from pain associated with ischemia and may provide at least temporary revascularization of the region with blood flow into the channels from the ventricle. Non-infrared detection device embodiments may utilize independent laser based treatment devices advanced through the lumen 13 of the monitoring catheter 14 after the ischemia is identified.

After detection and treatment of an ischemic region of tissue its recovery progress can be monitored by the present invention. Specifically, any of the above described ischemia detection devices may be reinserted into the patient to the area of interest and its thermal recovery time monitored. A thermal recovery time that is reduced in comparison to the recovery time recorded on the ischemic area was first identified would indicate increased blood flow to the region and successful treatment. Frequency of the subsequent monitoring can be dictated by the physician.

It should be understood, however, that the foregoing description of the invention is intended merely to be illustrative thereof and that other modifications, embodiments and equivalents may be apparent to those skilled in the art without departing from its spirit.

Having thus described the invention what we desire to claim and secure by Letters Patent is:

1. An ischemia detection device for tissue comprising:
   a catheter having proximal and distal ends, at least one lumen, and having a temperature alteration mechanism configured to alter the temperature of a finite section of tissue;
   a temperature detector disposed at the distal end of the catheter configured to monitor the thermal response of the tissue over an interval of time; and
   a temperature display configured to display temperature data collected by the temperature detector over an interval of time.

2. The device of claim 1 wherein the temperature alteration mechanism of the catheter uses electrical resistance energy to heat the tissue.

3. The device of claim 1 further comprising an obturator located within the catheter, said obturator having proximal and distal ends and being adapted to penetrate the tissue.

4. An ischemia detection device as defined in claim 3 wherein the obturator comprises electrically conductive material and at least a portion of the obturator serves as an electrical lead for the temperature detector.

5. The device of claim 1 wherein the temperature detector comprises at least one thermal sensor located adjacent to the distal end of the obturator.

6. The device of claim 1 wherein the catheter has at least one radially projecting finger extending from the distal end of the catheter configured to contact the surface of the tissue.

7. The device of claim 5 wherein the temperature detector comprises at least one thermal sensor at the distal end of at least one radially projecting finger.

8. An ischemia detection device comprising:
   a catheter having proximal and distal ends, at least one lumen, and having a temperature alteration mechanism configured to alter the temperature of a finite section of tissue;
   a temperature detector disposed at the distal end of the catheter comprising an optical fiber and an infrared detector configured to transmit temperature data concerning the tissue that can be used to produce a thermal profile display; and
   a temperature display configured to display data collected by the temperature detector.

9. The device of claim 8 wherein the temperature display comprises a representation of the thermal profile of the tissue with temperature variations indicated by varying colors.

10. The device of claim 8 wherein the temperature alteration mechanism comprises a lumen of the catheter configured to transmit a fluid at a temperature other than body temperature from the proximal to the distal end of the catheter and a pressurizable source of the fluid joined to the lumen.

11. A device for detecting ischemia in the myocardium comprising:
a catheter having at least one lumen and proximal and distal ends and adapted to deliver a temperature-altering fluid to the myocardium;
an optical fiber having proximal and distal ends disposed within the catheter; and
an infrared detector connected to the proximal end of the optical fiber for receiving data transmitted from the optical fiber and displaying it as a profile of the temperature of the tissue.

12. A device for detecting and treating ischemia in the myocardium comprising:
a catheter having at least one lumen and proximal and distal ends and adapted to deliver a temperature-altering fluid to the myocardium;
an inner shaft having an obturator at one end disposed within the catheter, said obturator having proximal and distal ends at least one thermal sensor capable of transmitting data concerning the temperature of a finite section of tissue adjacent to its distal end; and
an angiogenic implant releasably disposed within the catheter configured to be implanted in the myocardium;
a temperature display configured to display data collected by the thermal sensor.

13. The device of claim 12 wherein the distal tip of the obturator is adapted to penetrate the myocardium.

14. The device of claim 12 wherein the temperature display shows the temperature of a finite section of tissue over an interval of time.

15. A method of detecting ischemia in myocardial tissue comprising:
providing a catheter;
using the catheter to alter the temperature of a finite section of tissue;
monitoring the thermal recovery time of the section of tissue returning to its original temperature after temperature alteration; and
repeating this procedure on another finite section of tissue so as to observe the difference in thermal response between ischemic and non-ischemic tissue sections.

16. The method of claim 15 also comprising the additional step of inserting an obturator having at least one thermal sensor through the guide catheter and bringing the distal tip of said obturator into contact with the patient's myocardium so that the thermal sensors of the obturator function as the temperature detection means.

17. The method of claim 15 also including the additional step of delivering an angiogenic implant through the lumen of the catheter into a target location of the patient's myocardium.

18. A method of detecting ischemia in myocardial tissue as defined in claim 15 wherein the thermal recovery time of the tissue is monitored at a location beneath the surface of the tissue.

19. A method of detecting ischemia in tissue comprising:
providing a catheter having an optical fiber and at least one lumen;
navigating a catheter through the vascular system of the patient;
delivering a fluid capable of either heating or cooling a finite section of the tissue; and
creating a thermal image of the temperature profile of the tissue section using the optical fiber located within the catheter.

20. A method of detecting ischemia in tissue as defined in claim 19 wherein the fluid has an amount of thermal energy that serves to heat the tissue above its normal temperature.

21. A method of detecting ischemia in tissue as defined in claim 19 wherein the fluid has a thermal energy capable of cooling the tissue below its normal temperature.

22. A method of detecting ischemia in tissue comprising:
providing a catheter having an optical fiber and at least one lumen;
navigating a catheter through a predetermined path in the patient's vascular system;
delivering a temperature alteration means through the catheter;
using a temperature detection means disposed within the lumen of the catheter to obtain a series of temperature readings showing the thermal response of the tissue; and
using a temperature display means to display the data collected by the temperature detection means.

23. A method of detecting ischemia as defined in claim 22 wherein the temperature detection means comprises an optical fiber and the optical fiber is inserted through the lumen of the catheter after the temperature alteration means has been delivered through the lumen of the catheter.

24. A method of monitoring the progress of angiogenesis comprising:
navigating a catheter having: at least one lumen, a proximal end, and a distal end through the vascular system of a patient to the myocardium, said catheter adapted to deliver a fluid bolus capable of altering the temperature of a finite section of the myocardium;
delivering a fluid bolus adjacent the myocardium capable of altering the temperature of a finite section of the myocardium;
using a temperature detector disposed within the lumen of the catheter to obtain a series of temperature readings showing the thermal response of a finite section of the myocardium after delivery of the fluid bolus; and
using a temperature display to display the thermal response of the finite section of the myocardium by using the data collected by the temperature detector.

25. The method of claim 24 wherein the temperature detector comprises an infrared optical fiber and the temperature display creates a thermal image showing areas of the myocardium having different temperatures by using varying colors.

26. The method of claim 24 wherein the temperature detector comprises at least one thermal sensor located adjacent to the distal end of an obturator residing within the catheter and the temperature display shows a plot of temperature readings for a finite section of the myocardium taken over series of time intervals so as to allow differentiation between normal and ischemic tissue by observing the difference in thermal responses.

27. A method of detecting ischemia in tissue comprising:
altering the temperature of a finite section of tissue;
monitoring the change in temperature of the finite section of tissue as a function of time; and
displaying the temperature of the tissue as it changes over time so as to permit observation of the differences in response of normal and ischemic tissue.

28. A method of detecting and treating ischemia in tissue comprising:
  altering the temperature of a finite section of tissue;
  recording the change in temperature of the finite section of tissue as a function of time;
  displaying the temperature so as to permit observation of the differences in response of normal and ischemic tissue; and
  implanting an angiogenic implant in the ischemic tissue.

29. A method of treating ischemia comprising:
  identifying ischemic tissue by obtaining and evaluating thermal information regarding an area of tissue;
  treating identified ischemic tissue with means to initiate revascularization of the tissue;
  monitoring the tissue after treatment by observing and evaluating thermal information regarding the tissue.

30. A method of treating ischemia as defined in claim 29 wherein
  the means to initiate revascularization comprises a therapeutic agent that is delivered to the tissue.

31. A method of treating ischemia as defined in claim 29 wherein the means to initiate revascularization of the tissue comprises channels formed into the tissue.

32. An ischemia detection device comprising:
  means for collecting thermal information determinative of the location of the ischemic tissue; and
  means for treating the ischemic tissue.

* * * * *